United States Patent
Xu et al.

(10) Patent No.: US 10,772,933 B2
(45) Date of Patent: Sep. 15, 2020

(54) MEDICAMENT FOR TREATING PULMONARY TUBERCULOSIS

(71) Applicant: Shandong Zhonghai Pharmaceutical CO. LTD, Weifang (CN)

(72) Inventors: Baozhen Xu, Weifang (CN); Qian Cheng, Weifang (CN); Long Cheng, Weifang (CN)

(73) Assignee: SHANDONG ZHONGHAI PHARMACEUTICAL CO. LTD, Weifang (CN)

( * ) Notice: Subject to any disclaimer, the term of this patent is extended or adjusted under 35 U.S.C. 154(b) by 0 days.

(21) Appl. No.: 16/073,887

(22) PCT Filed: Jan. 20, 2017

(86) PCT No.: PCT/CN2017/071822
§ 371 (c)(1),
(2) Date: Jul. 30, 2018

(87) PCT Pub. No.: WO2017/129052
PCT Pub. Date: Aug. 3, 2017

(65) Prior Publication Data
US 2019/0038711 A1  Feb. 7, 2019

(30) Foreign Application Priority Data
Jan. 29, 2016 (CN) .......................... 2016 1 0061751

(51) Int. Cl.
| | | |
|---|---|---|
| A61K 38/02 | (2006.01) | |
| A61K 38/16 | (2006.01) | |
| A61K 36/04 | (2006.01) | |
| A61K 36/05 | (2006.01) | |
| A61K 36/315 | (2006.01) | |
| A61K 31/715 | (2006.01) | |
| A61K 36/428 | (2006.01) | |
| A61K 36/03 | (2006.01) | |
| A61P 31/06 | (2006.01) | |
| A61K 31/351 | (2006.01) | |
| A61K 36/195 | (2006.01) | |
| A61K 36/8945 | (2006.01) | |

(52) U.S. Cl.
CPC .......... *A61K 38/168* (2013.01); *A61K 31/351* (2013.01); *A61K 31/715* (2013.01); *A61K 36/03* (2013.01); *A61K 36/04* (2013.01); *A61K 36/05* (2013.01); *A61K 36/195* (2013.01); *A61K 36/315* (2013.01); *A61K 36/428* (2013.01); *A61K 36/8945* (2013.01); *A61P 31/06* (2018.01)

(58) Field of Classification Search
None
See application file for complete search history.

(56) References Cited

U.S. PATENT DOCUMENTS

2005/0196410 A1 * 9/2005 Daniels ................ A61K 31/198
424/195.17

FOREIGN PATENT DOCUMENTS

| | | |
|---|---|---|
| CN | 101760492 A | 6/2010 |
| CN | 105535927 A | 5/2016 |
| CN | 105535954 A | 5/2016 |
| CN | 105582522 A | 5/2016 |
| CN | 105597080 A | 5/2016 |
| CN | 105597081 A | 5/2016 |
| CN | 105617354 A | 6/2016 |
| CN | 105617355 A | 6/2016 |
| CN | 105617356 A | 6/2016 |
| CN | 105641681 A | 6/2016 |
| CN | 105709206 A | 6/2016 |
| CN | 105709207 A | 6/2016 |

OTHER PUBLICATIONS

Hidari et al (Biochemical and biophysical research communications, (Nov. 7, 2008) vol. 376, No. 1, pp. 91-5).*
Abdel-Fattah et al (Phytochemistry (Oxford), (1987) vol. 26, No. 5, pp. 1447-1448).*
https://tcmwiki.com/wiki/ningpo-yam-rhizome 2011.*
https://tcmwiki.com/wiki/fructus-trichosanthis 2011.*
https://www.alibaba.com/product-detail/Natural-Shan-Yao-Organic-Food-Grade_60824206208.html 2011.*
https://tcmwiki.com/wiki/indigo-naturalis 2011.*
Sharif et al (American Journal of Drug Delivery and Therapeutics. Prolific Anticancer Bioactivity of Algal Extracts (Review) pp. 1-13 Cell 3:8 • Jan. 2014).*
Li et al (Mol Biotech. 2011 47: 105-110).*
Garrison et al (Antiviral Res. Dec. 2014. 0: 1-7).*
Nuhu, A. (Journal of Marine Biology. vol. 2013, pp. 1-8, Article ID 325636).*
Hiroe Go et al., A glycoprotein from Laminaria japonica induces apoptosis in HT-29 colon cancer cells, Toxicology in Vitro, vol. 24, No. 6, Jul. 6, 2010.

* cited by examiner

*Primary Examiner* — Jennifer E Graser
(74) *Attorney, Agent, or Firm* — Bayramoglu Law Office LLC

(57) ABSTRACT

A medicament for use in treating tuberculosis, the medicament is a glycoprotein, a mixture of polysaccharide and protein, a polypeptide or a protein.

1 Claim, No Drawings

MEDICAMENT FOR TREATING PULMONARY TUBERCULOSIS

CROSS REFERENCE TO RELATED APPLICATIONS

This application is the national phase entry of International Application No. PCT/CN2017/071822, filed on Jan. 20, 2017, which is based upon and claims priority to Chinese Patent Application No. 201610061751.3, filed on Jan. 29, 2016, the entire contents of which are incorporated herein by reference.

TECHNICAL FIELD

The present invention relates to a medicament for use in treating tuberculosis and belongs to the technical field of medicine.

BACKGROUND

Tuberculosis is a chronic infectious disease, which does not necessarily break out after infection. Even though it breaks out, there may be no symptom appearing immediately. Generally, this disease may break out after several months, years, even decades. Therefore, it is difficult to find tuberculosis in its early stage. Tuberculosis may break out all the year round. The adolescents of 15-35 years old would be at high risk of tuberculosis and may suffer from tuberculosis complicated with diabetes and tuberculosis in pregnancy.

Tuberculosis can be classified into 5 types: Type I, primary tuberculosis, having the syndromes of primary focus in lungs, drainage lymphangitis, pulmonary hilum and/or mediastinal lymphatic tuberculous inflammation; Type II, disseminated tuberculosis, acute, sub-acute and chronic; Type III, infiltrating tuberculosis, manifested as exudative-mainly exudative lesions, proliferation-mainly proliferative lesions, and caseation-including tuberculosis with caseous foci developed from the previous two tuberculosis, caseous pneumonia, and cavities and tuberculoma; Type IV, chronic fibro-cavitative tuberculosis, developed from the infiltrative tuberculosis and having the following pathological characteristics: the wall of the cavity being surrounded by thick fibrous tissue, with visible disseminated foci and repairing fibrous tissue, the pulmonary lobe where the focus is located shrinking, the trachea and the mediastinum moving toward the diseased side, and the remaining lung exhibiting compensatory emphysema; Type V, tuberculous pleurisy.

Traditional Chinese medicine holds that the causes of tuberculosis (phthisis) are nothing more than internal and external causes. The external cause is infection, and the internal cause is deficiency of both Qi and blood, and depletion of Yin and essence. Since the healthy Qi of a person is damaged first and the body of the person is weak without recovery, the *Mycobacterium Tuberculosis* can invade the weak body and erode the lungs, leading to the deficiency of lung yin. Due to heat impairing pulmonary collaterals, the symptoms of dry cough, hemoptysis, pharynx dryness and the like will appear." "The body fluid cannot be distributed in case of lung deficiency, and therefore, kidneys may lose the source of life and thus be also affected by the disease. In case of the deficiency of kidney yin and the disturbance of deficiency fire, the symptoms of hectic fever and hot flash, dream emission for men and amenorrhea for women may appear. Moreover, due to the deficiency of kidney-yin, hyperactivity of heart-liver fire and ascending of the heart-liver fire to the lungs to further deplete lung Yin, the symptoms of night sweat and insomnia, dysphoria and rage susceptibility, pain in chest and hypochondrium and the like will appear." Further, the lung deficiency may hinder self-nourishing of mother Qi, so that spleens can be affected by the disease too. For deficient spleen and weak vital energy, the symptoms of short of breath, weakness, poor appetite, loose stool and the like will appear."

Western medicine holds that *Mycobacterium Tuberculosis* is the pathogen of tuberculosis. The *Mycobacterium Tuberculosis* is a kind of branching bacteria which are less than 4 μm long and less than 0.6 μm wide. The *Mycobacterium Tuberculosis* is classified into human type, bovine type, rat type and the like, among which the human type is mainly pathogenic to human. Patients with tuberculosis are classified into two types: open and non-open. The phlegm of open patients contains *Mycobacterium Tuberculosis*, and the *Mycobacterium Tuberculosis* may infect others via droplet when the patient coughs or sneezes. The open patients are in the minority. The phlegm of non-open patients contains no *Mycobacterium Tuberculosis*, and the non-open patients are in the majority. However, an open patient may have an interactive relation with a non-open patient. When an infectious tuberculosis patient (open) coughs or sneezes, the sputum containing the *Mycobacterium Tuberculosis* are spread into the air as droplet. When people having lowered immunity inhales the *Mycobacterium Tuberculosis*, the *mycobacterium tuberculosis* may have the opportunity to propagate in lungs to infect the lungs.

At present, most medicaments for treating tuberculosis are western medicines. Although western medicines can kill the *Mycobacterium Tuberculosis*, but the resistance and tolerance of the *Mycobacterium Tuberculosis* to medicines will be improved because of mutations of the *Mycobacterium Tuberculosis*, resulting in significant reduction in pharmaceutical effects of the western medicines after use for a period of time. In addition, the western medicines may have strong toxic and side effects with damage to the patients' health, reducing the constitution and the immunity of the patients and leading to a reduced therapeutic effect and a prolonged course of treatment. The current Chinese herbal medicines for the treatment of tuberculosis are low in toxic and side effects, but have the defects of slow effect, long course of treatment and low cure rate.

SUMMARY

In order to solve the problems in the prior art, the present invention provides a medicament for use in treating tuberculosis to achieve the following objectives of the invention.

(1) The medicament of the present invention has a good treatment effect on tuberculosis. After three months of treatment, the sputum negative conversion rate of 80.2-90.6%, the focus absorption rate of 60.3-73.2% and the cavity closure rate of 62.5-73.4% could be achieved.

(2) The medicament of the present invention reduces the number of bacterial colonies in lungs and spleens. After three months of treatment, number of bacterial colonies in lungs of mice could be reduced to $52.6\text{-}82.3 \times 10^4$ CFU, and the number of the bacterial colonies in spleens of mice could be reduced to $2.43\text{-}3.68 \times 10^4$ CFU.

(3) The medicament of the present invention increases the number of T lymphocytes CD4+T of mice, increase the thymus index of mice and increase the content of IFN-γ of multi-drug resistant tuberculosis mice. After three months of treatment, the number of CD4+T could reach 27.52-30.25/

µL and the thymic weight index could reach 0.225-0.246. In addition, the content of IFN-γ could reach 67.58-69.89 ng/mL.

In Order to Solve the Aforesaid Problems, the Present Invention Adopts the Following Technical Solution:

The medicament for treating tuberculosis, the medicament being a glycoprotein, a mixture of a polysaccharide and a protein, a polypeptide or a protein, wherein the glycoprotein comprises 1%-99% of saccharide and 1%-99% of protein by weight; and the mixture of a polysaccharide and a protein comprises 1%-99% of saccharide and 1%-99% of protein by weight. A molecular weight of the alga glycoprotein is 0.2-3000 kDa.

The following are further modifications to the above technical solutions.

The medicament is a marine algal glycoprotein.

The marine algal glycoprotein comprises 1%-99% of saccharide and 1%-99% of protein by weight; and the mixture of a marine algae polysaccharide and protein comprises 1%-99% of saccharide and 1%-99% of protein by weight.

The marine algal glycoprotein has a molecular weight of 0.2-3000 kDa.

The polysaccharide in the mixture of polysaccharide and protein has a molecular weight of 0.2-3000 kDa; the protein in the mixture of algae polysaccharide and protein has a molecular weight of 0.2-3000 kDa.

The medicament comprises, by weight, 1-99 portions of glycoprotein and 1-25 portions of glucuronic acid.

The medicament comprises, by weight, 1-99 portions of marine algal glycoprotein and –27 portions of glucuronic acid.

The medicament comprises, by weight, 1-99 portions of marine algal glycoprotein, 1-31 portions of glucuronic acid, and 2-11 portions of indigo naturalis.

The marine algae is one of blue-green algae, green algae, red algae, gold algae and brown algae.

The medicament comprises, by weight, 1-99 portions of marine algal glycoprotein, 5-15 portions of indigo naturalis, 6-16 portions of Ningpo yam rhizome and 1-17 portions of glucuronic acid by weight.

The medicament comprises, by weight, 1-99 portions of marine algal glycoprotein, 5-15 portions of indigo naturalis, 6-16 portions of Ningpo yam rhizome, 7-17 portions of *fructus trichosanthis* and 8-14 portions of cicada slough.

The medicament comprises, by weight, 1%-99% of saccharide and 1%-99% of protein.

The marine algal glycoprotein comprises, by weight, 1%-99% of saccharide and 1%-99% of protein.

Compared with the Prior Art, the Advantages in the Present Invention are:—

(1) The medicament of the present invention has a good treatment effect on tuberculosis. After three months of treatment, the sputum negative conversion rate of 80.2-90.6%, the focus absorption rate of 60.3-73.2% and the cavity closure rate of 62.5-73.4% could be achieved.

(2) The medicament of the present invention could reduce the number of bacterial colonies in lungs and spleens. After three months of treatment, the number of bacterial colonies in lungs of mice could be reduced to $52.6$-$82.3 \times 10^4$ CFU, and the number of the bacterial colonies in spleens of mice could be reduced to $2.43$-$3.68 \times 10^4$ CFU.

(3) The medicament of the present invention could increase the number of T lymphocytes CD4+T of mice, increase the thymus index of mice and increase the content of IFN-γ of multi-drug resistant tuberculosis mice. After three months of treatment, the number of CD4+T could reach 27.52-30.25/µL and the thymic weight index could reach 0.225-0.246. In addition, the content of IFN-γ could reach 67.58-69.89 ng/mL.

DETAILED DESCRIPTION OF THE EMBODIMENTS

The preferred embodiments of the present invention will be illustrated below, and the preferred embodiments described herein are merely intended to illustrate and explain the invention, but not limited to this invention.

Embodiment 1

A Medicament for Use in Treating Tuberculosis

Wherein the medicament is a marine algal glycoprotein;
the marine algal glycoprotein comprises 1% saccharide and 99% protein by weight;
the molecular weight is 0.2 kDa;
the marine algae is blue-green algae;
the saccharide is a polysaccharide;
the polysaccharide comprises xylose, fucose, arabinose, glucose, galactose, mannose, and rhamnose;
the protein comprises asparaginate, cysteine, lysine, arginine, serine, and threonine.

Embodiment 2

A Medicament for Use in Treating Tuberculosis

Wherein the medicament is a marine algal glycoprotein;
the marine algal glycoprotein comprises 6% saccharide and 85% protein by weight;
the molecular weight is 25 kDa;
the marine algae is blue-green algae;
the saccharide is a polysaccharide;
the polysaccharide comprises xylose, fucose, arabinose, glucose, galactose, mannose, and rhamnose;
the protein comprises asparaginate, cysteine, lysine, arginine, serine, and threonine.

Embodiment 3

A Medicament for Use in Treating Tuberculosis

Wherein the medicament is a marine algal glycoprotein;
the marine algal glycoprotein comprises 31% saccharide and 64% protein by weight;
the molecular weight is 3 kDa;
the marine algae is blue-green algae;
the saccharide is a polysaccharide;
the polysaccharide comprises xylose, fucose, arabinose, glucose, galactose, mannose, and rhamnose;
the protein comprises asparaginate, cysteine, lysine, arginine, serine, and threonine.

Embodiment 4

A Medicament for Use in Treating Tuberculosis

Wherein the medicament is a marine algal glycoprotein;
the marine algal glycoprotein comprises 55% saccharide and 40% protein by weight;
the molecular weight is 94 kDa;
the marine algae is red algae;
the saccharide is a polysaccharide;
the polysaccharide comprises xylose, fucose, arabinose, glucose, galactose, mannose, and rhamnose;

the protein comprises asparaginate, cysteine, lysine, arginine, serine, and threonine.

Embodiment 5

A Medicament for Use in Treating Tuberculosis
Wherein the medicament is a marine algal glycoprotein;
the marine algal glycoprotein comprises 71% saccharide and 23% protein by weight;
the molecular weight is 150 kDa;
the marine algae is brown algae;
the saccharide is a polysaccharide;
the polysaccharide comprises xylose, fucose, arabinose, glucose, galactose, mannose, and rhamnose;
the protein comprises asparaginate, cysteine, lysine, arginine, serine, and threonine.

Embodiment 6

A Medicament for Use in Treating Tuberculosis
Wherein the medicament is a marine algal glycoprotein;
the marine algal glycoprotein comprises 99% saccharide and 1% protein by weight;
the molecular weight is 3000 kDa;
the marine algae is gold algae;
the saccharide is a polysaccharide;
the polysaccharide comprises xylose, fucose, arabinose, glucose, galactose, mannose, and rhamnose;
the protein comprises asparaginate, cysteine, lysine, arginine, serine, and threonine.

The glycoprotein as described in the above Embodiments 1-6 further includes a pigment; the pigment is a natural pigment contained in an algal substances.

The above Embodiments 1-6 could be summarized as:
A Medicament for Use in Treating Tuberculosis
Wherein the medicament is a glycoprotein;
the glycoprotein comprises, by weight, 1%-99% of saccharide and 1%-99% of protein;
the molecular weight of the glycoprotein is 0.2-30000 kDa;
the saccharide is a polysaccharide;
the medicament comprises synthetic glycoprotein, synthetic polysaccharide and synthetic protein.

The protein comprises 20 kinds of amino acids and 8 kinds of synthetic amino acids.

The preparation method of the medicament: the glycoprotein is prepared into capsules and tablets etc. according to a conventional process; the mixture of the polysaccharide and the protein is prepared into capsules and tablets etc. according to a conventional process.

Embodiment 7

Application of the Medicament in the Treatment of Tuberculosis

An experimental method comprises the following steps: selecting mice, disinfecting the tails by using 75% alcohol, intravenously injecting 0.2 ml of 5 mg/ml *Mycobacterium Tuberculosis* suspension into each mouse, compressing the puncture positions for stopping bleeding 1 minute after injection, observing for one day after animal modeling, and if there was pale swelling in the tails of the mice or the tails had local necrosis and fell off, indicating that the liquid was not completely injected into the blood vessels of the tails of the mice and sacrificing such mice; finally, selecting satisfactory mice and randomly dividing the mice into groups, 12 mice in each group, including a model control group, and groups 1-6 of the present invention; additionally, randomly selecting 12 mice as blank control group.

Administration was performed on the second day after modeling. The groups of the present invention were provided with the medicament as described in examples 1-6 of the present invention at the dose of 3 g/day, three times a day, by means of intragastric administration continuously for 28 days. The blank control group and the model control group were intragastrically provided with normal saline of the same volume. Various indexes were measured 3 months days after the administration.

Organ index=organ weight/mouse weight

TABLE 1

Therapeutic effects after three months

| | Sputum negative conversion rate (%) | Focus absorption rate (%) | Cavity closure rate (%) | Number of bacterial colonies in lungs (×10⁴CFU) | Number of bacterial colonies in spleens (×10⁴CFU) |
|---|---|---|---|---|---|
| Model control group | — | — | — | 123.5 | 5.98 |
| Embodiment 1 | 80.2 | 60.3 | 62.5 | 82.3 | 3.68 |
| Embodiment 2 | 85.6 | 68.9 | 66.8 | 62.3 | 2.98 |
| Embodiment 3 | 90.6 | 73.2 | 73.4 | 52.6 | 2.43 |
| Embodiment 4 | 86.6 | 70.3 | 71.2 | 63.4 | 2.65 |
| Embodiment 5 | 83.8 | 69.1 | 68.4 | 72.9 | 2.71 |
| Embodiment 6 | 81.6 | 62.3 | 63.4 | 80.9 | 3.26 |

The medicament of the present invention has a good treatment effect on tuberculosis. The sputum negative conversion rate of 80.2-90.6%, the focus absorption rate of 60.3-73.2%, and the cavity closure rate of 62.5-73.4% has been achieved. The number of bacterial colonies in lungs and spleens could be reduced.

The number of bacterial colonies in lungs could be $19.5 \times 10^4$ CFU, and the number of the bacterial colonies in spleens could be $0.8 \times 10^4$ CFU.

TABLE 2

Effects of the medicament of the present invention on the T lymphocytes CD4 + T, the thymic weight index and the cytokines IFN-γ of mice

| | CD4 + T/μL | Thymic weight index | IFN-γ ng/mL |
|---|---|---|---|
| Blank control group | 41.57 ± 5.68 | 0.323 ± 0.040 | 121.85 ± 14.2 |
| Model control group | 24.56 ± 8.59 | 0.205 ± 0.052 | 65.21 ± 10.42 |
| Embodiment 1 | 27.52 ± 7.56 | 0.225 ± 0.043 | 67.58 ± 11.26 |
| Embodiment 2 | 29.56 ± 6.89 | 0.236 ± 0.056 | 69.25 ± 10.89 |
| Embodiment 3 | 30.25 ± 7.23 | 0.246 ± 0.052 | 69.89 ± 11.36 |
| Embodiment 4 | 28.12 ± 6.59 | 0.240 ± 0.048 | 69.06 ± 12.56 |
| Embodiment 5 | 28.43 ± 6.45 | 0.232 ± 0.053 | 68.23 ± 12.65 |
| Embodiment 6 | 28.00 ± 7.02 | 0.228 ± 0.049 | 67.69 ± 12.05 |

The medicament of the present invention can increase the number of T lymphocytes CD4+T of mice, increase the thymus index of mice and increase the content of IFN-γ of multi-drug resistant tuberculosis mice. IFN-γ is the key of effective antibacterial immunity, which attract and gather monocytes/macrophagocytes to enhance its effect of killing the multi-drug resistant *Mycobacterium Tuberculosis*. The number of CD4+T could be 27.52-30.25/μL and the thymic weight index could be 0.225-0.246. In addition, the content of IFN-γ could be 67.58-69.89 ng/mL.

Embodiment 8

A Medicament for Use in Treating Tuberculosis

The medicament comprises, by weight, 1 portion of marine algal glycoprotein and 1 portion of glucuronic acid.

The marine algal glycoprotein comprises 11% saccharide and 85% protein by weight;
the molecular weight is 8 kDa;
the marine algae is *spirulina*;
the saccharide is a polysaccharide;
the polysaccharide comprises xylose, fucose, arabinose, glucose, galactose, mannose, and rhamnose;
the protein comprises asparaginate, cysteine, lysine, arginine, serine, and threonine.

Embodiment 9

A Medicament for Use in Treating Tuberculosis

Similar to Embodiment 8, only the proportions of the marine algal glycoprotein and the glucuronic acid by weight are changed as follows:
the medicament comprises, by weight, 36 portions of marine algal glycoprotein and 7 portions of glucuronic acid.

Embodiment 10

A Medicament for Use in Treating Tuberculosis

Similar to Embodiment 8, only the proportions of the marine algal glycoprotein and the glucuronic acid by weight are changed as follows:
the medicament comprises, by weight, 68 portions of marine algal glycoprotein and 13 portions of glucuronic acid.

Embodiment 11

A Medicament for Use in Treating Tuberculosis

Similar to Embodiment 8, only the proportions of the marine algal glycoprotein and the glucuronic acid by weight are changed as follows:
the medicament comprises, by weight, 99 portions of marine algal glycoprotein and 27 portions of glucuronic acid.

Embodiment 12

A Medicament for Use in Treating Tuberculosis

The medicament comprises, by weight, 1 portion of marine algal glycoprotein, 1 portion of glucuronic acid and 2 portions of indigo naturalis;
the marine algal glycoprotein comprises 23% saccharide and 79% protein by weight;
the molecular weight of the marine algal glycoprotein is 12 kDa;
the marine algae is *chlorella*;
the saccharide is a polysaccharide;
the polysaccharide comprises xylose, fucose, arabinose, glucose, galactose, mannose, and rhamnose;
the protein comprises asparaginate, cysteine, lysine, arginine, serine, and threonine.

Embodiment 13

A Medicament for Use in Treating Tuberculosis

Similar to Embodiment 2, only the proportions of the marine algal glycoprotein, the glucuronic acid and indigo naturalis by weight are changed as follows:
the medicament comprises, by weight, 34 portions of marine algal glycoprotein, 10 portions of glucuronic acid and 5 portions of indigo naturalis.

Embodiment 14

A Medicament for Use in Treating Tuberculosis

Similar to Embodiment 12, only the proportions of the marine algal glycoprotein, the glucuronic acid and indigo naturalis by weight are changed as follows:
the medicament comprises, by weight, 58 portions of marine algal glycoprotein, 22 portions of glucuronic acid and 9 portions of indigo naturalis.

Embodiment 15

A Medicament for Use in Treating Tuberculosis

Similar to Embodiment 12, only the proportions of the marine algal glycoprotein, the glucuronic acid and indigo naturalis by weight are changed as follows:
the medicament comprises, by weight, 99 portions of marine algal glycoprotein, 31 portions of glucuronic acid and 11 portions of indigo naturalis.

Application of the Medicament as Described in the Above Embodiment 8 to Embodiment 15 in the Treatment of Tuberculosis:

Using the test method of Embodiment 7, the medicament of Embodiment 8-Embodiment 15 in this invention groups have the following application effects:

TABLE 3

Therapeutic effects after three months

| | Sputum negative conversion rate (%) | Focus absorption rate (%) | Cavity closure rate (%) | Number of bacterial colonies in lungs (×10$^4$CFU) | Number of bacterial colonies in spleens (×10$^4$CFU) |
|---|---|---|---|---|---|
| Model control group | — | — | — | 123.5 | 5.98 |
| Embodiment 8 | 87.2 | 71.3 | 72.5 | 50.3 | 2.28 |
| Embodiment 9 | 87.6 | 72.9 | 73.8 | 49.8 | 2.13 |
| Embodiment 10 | 93.3 | 79.2 | 80.4 | 30.5 | 1.33 |
| Embodiment 11 | 87.3 | 72.3 | 73.6 | 48.4 | 2.05 |
| Embodiment 12 | 86.9 | 73.5 | 74.6 | 48.5 | 2.03 |
| Embodiment 13 | 86.7 | 73.3 | 74.7 | 49.9 | 2.15 |
| Embodiment 14 | 94.5 | 79.0 | 80.2 | 31.9 | 1.25 |
| Embodiment 15 | 87.2 | 73.4 | 75.0 | 48.6 | 1.98 |

TABLE 4

Effects of the medicament of the present invention on the T lymphocytes CD4 + T, the thymic weight index and the cytokines IFN-γ of mice

|  | CD4 + T/μL | Thymic weight index | IFN-γ ng/mL |
|---|---|---|---|
| Blank control group | 41.57 ± 5.68 | 0.323 ± 0.040 | 121.85 ± 14.2 |
| Model control group | 24.56 ± 8.59 | 0.205 ± 0.052 | 65.21 ± 10.42 |
| Embodiment 8 | 33.52 ± 6.56 | 0.255 ± 0.043 | 69.58 ± 10.26 |
| Embodiment 9 | 34.56 ± 6.25 | 0.256 ± 0.056 | 70.25 ± 11.89 |
| Embodiment 10 | 40.25 ± 7.06 | 0.315 ± 0.050 | 74.89 ± 10.36 |
| Embodiment 11 | 33.12 ± 6.79 | 0.248 ± 0.049 | 70.06 ± 11.56 |
| Embodiment 12 | 34.43 ± 6.65 | 0.247 ± 0.043 | 70.23 ± 11.65 |
| Embodiment 13 | 33.20 ± 7.12 | 0.252 ± 0.044 | 70.69 ± 12.05 |
| Embodiment 14 | 41.89 ± 6.59 | 0.313 ± 0.051 | 74.23 ± 11.36 |
| Embodiment 15 | 32.56 ± 6.26 | 0.255 ± 0.044 | 70.28 ± 10.36 |

In Embodiments 8-11, only the weight ratio of the marine algal glycoprotein and the glucuronic acid was changed. From the experimental results, Embodiment 10 is the most preferred example.

In Embodiments 12-15, only the weight ratio of the marine algal glycoprotein, the glucuronic acid and indigo naturalis was changed. From the experimental results, Embodiment 14 is the most preferred example.

Embodiment 16

A Medicament for Use in Treating Tuberculosis

The medicament comprises, by weight, 1 portion of marine algal glycoprotein, 5 portions of indigo naturalis, 6 portions of *dioscorea nipponica*, and 1 portion of glucuronic acid.

The marine algal glycoprotein comprises 26% saccharide and 74% protein by weight;
 the molecular weight is 8 kDa;
 the marine algae is *nostoc flagelliforme*;
 the saccharide is a polysaccharide;
 the polysaccharide comprises xylose, fucose, arabinose, glucose, galactose, mannose, and rhamnose;
 the protein comprises asparaginate, cysteine, lysine, arginine, serine, and threonine.

Embodiment 17

A Medicament for Use in Treating Tuberculosis

Similar to Embodiment 16, only the proportions of the marine algal glycoprotein, indigo naturalis, *dioscorea nipponica* and the glucuronic acid by weight are changed as follows:
 the medicament comprises, by weight, 49 portions of marine algal glycoprotein, 8 portions of indigo naturalis, 11 portions of *dioscorea nipponica*, and 8 portions of glucuronic acid.

Embodiment 18

A Medicament for Use in Treating Tuberculosis

Similar to Embodiment 16, only the proportions of the marine algal glycoprotein, indigo naturalis, *dioscorea nipponica* and the glucuronic acid by weight are changed as follows:

the medicament comprises, by weight, 99 portions of marine algal glycoprotein, 15 portions of indigo naturalis, 16 portions of *dioscorea nipponica*, and 17 portions of glucuronic acid.

Embodiment 19

A Medicament for Use in Treating Tuberculosis

The medicament comprises, by weight, 1 portion of marine algal glycoprotein, 5 portions of indigo naturalis, 6 portions of Ningpo yam rhizome, 7 portions of *fructus trichosanthis* and 8 portions of cicada slough.

The marine algal glycoprotein comprises 41% saccharide and 59% protein by weight;
 the molecular weight is 12 kDa;
 the marine algae is laver;
 the saccharide is a polysaccharide;
 the polysaccharide comprises xylose, fucose, arabinose, glucose, galactose, mannose, and rhamnose;
 the protein comprises asparaginate, cysteine, lysine, arginine, serine, and threonine.

Embodiment 20

A Medicament for Use in Treating Tuberculosis

Similar to Embodiment 19, only the proportions of the marine algal glycoprotein, indigo naturalis, Ningpo yam rhizome, *fructus trichosanthis* and cicada slough by weight are changed as follows:
 the medicament comprises, by weight, 55 portions of marine algal glycoprotein, 14 portions of indigo naturalis, 9 portions of Ningpo yam rhizome, 15 portions of *fructus trichosanthis* and 10 portions of cicada slough.

Embodiment 21

A Medicament for Use in Treating Tuberculosis

Similar to Embodiment 19, only the proportions of the marine algal glycoprotein, indigo naturalis, Ningpo yam rhizome, *fructus trichosanthis* and cicada slough by weight are changed as follows:
 the medicament comprises, by weight, 99 portions of marine algal glycoprotein, 15 portions of indigo naturalis, 16 portions of Ningpo yam rhizome, 17 portions of *fructus trichosanthis* and 14 portions of cicada slough.

Application of the Medicament as Described in the Above Embodiment 16 to Embodiment 21 in Treating Tuberculosis:

Using the test method as described in Embodiment 7, the medicament as described in Embodiment 16-Embodiment 21 in this invention groups have the following application effects:

TABLE 5

Therapeutic effects after three months

|  | Sputum negative conversion rate (%) | Focus absorption rate (%) | Cavity closure rate (%) | Number of bacterial colonies in lungs (×10$^4$CFU) | Number of bacterial colonies in spleens (×10$^4$CFU) |
|---|---|---|---|---|---|
| Model control group | — | — | — | 123.5 | 5.98 |
| Embodiment 16 | 90.5 | 73.3 | 79.5 | 30.3 | 1.58 |

TABLE 5-continued

Therapeutic effects after three months

| | Sputum negative conversion rate (%) | Focus absorption rate (%) | Cavity closure rate (%) | Number of bacterial colonies in lungs (×10⁴CFU) | Number of bacterial colonies in spleens (×10⁴CFU) |
|---|---|---|---|---|---|
| Embodiment 17 | 95.3 | 85.9 | 85.8 | 20.8 | 0.83 |
| Embodiment 18 | 90.9 | 73.2 | 80.4 | 31.5 | 1.42 |
| Embodiment 19 | 91.3 | 76.3 | 79.6 | 31.4 | 1.46 |
| Embodiment 20 | 96.9 | 84.5 | 86.6 | 18.5 | 0.85 |
| Embodiment 21 | 91.7 | 77.3 | 79.7 | 32.9 | 16.5 |

TABLE 6

Effects of the medicament of the present invention on the T lymphocytes CD4 + T, the thymic weight index and the cytokines IFN-γ of mice

| | CD4 + ↑T/μL | Thymic weight index | IFN-γ ng/mL |
|---|---|---|---|
| Blank control group | 41.57 ± 5.68 | 0.323 ± 0.040 | 121.85 ± 14.2 |
| Model control group | 24.56 ± 8.59 | 0.205 ± 0.052 | 65.21 ± 10.42 |
| Embodiment 16 | 34.52 ± 5.46 | 0.285 ± 0.043 | 71.58 ± 10.58 |
| Embodiment 17 | 41.56 ± 6.75 | 0.325 ± 0.057 | 76.85 ± 11.34 |
| Embodiment 18 | 35.25 ± 7.46 | 0.296 ± 0.053 | 71.89 ± 10.36 |
| Embodiment 19 | 36.12 ± 6.99 | 0.288 ± 0.046 | 71.46 ± 11.58 |
| Embodiment 20 | 42.43 ± 6.35 | 0.328 ± 0.047 | 76.73 ± 11.34 |
| Embodiment 21 | 35.20 ± 7.22 | 0.272 ± 0.045 | 72.69 ± 10.05 |

In Embodiments 16-18, only the weight ratio of the marine algal glycoprotein, indigo naturalis, Ningpo yam rhizome and the glucuronic acid was changed. From the experimental results, Embodiment 17 is the most preferred embodiment.

In Embodiments 19-21, only the weight ratio of the marine algal glycoprotein, indigo naturalis, Ningpo yam rhizome, *fructus trichosanthis*, cicada slough, and the glucuronic acid was changed. From the experimental results, Embodiment 20 is the most preferred embodiment.

Embodiment 22

A Medicament for Use in Treating Tuberculosis

The medicament comprises the following components by weight:

70 portions of marine algal glycoprotein, 8 portions of *bulbus fritillariae*, 3 portions of *radix psammosilenes*, 7 portions of *radix acanthopanacis senticosi*, 5 portions of *herba inulae*, 3 portions of *flos inulae*, 8 portions of *radix ranunculi ternati*, 9 portions of *radix aconiti*, and 12 portions of *radix physochlainae*.

The marine algal glycoprotein comprises 10% saccharide and 80% protein by weight;

the molecular weight of the marine algal glycoprotein is 8 kDa;

the marine algae is blue-green algae;

the saccharide comprises the following components by weight: 16 portions of xylose, 12 portions of fucose, and 17 portions of arabinose;

the protein comprises the following components by weight: 19 portions of asparaginate, 13 portions of cysteine, and 19 portions of lysine.

Using the test method as described in Embodiment 7, the medicament as described in Embodiment 22 in this invention groups have the following application effects:

the medicament of the present invention has a good treatment effect on tuberculosis. The sputum negative conversion rate of 96.8%, the focus absorption rate of 86.3% and the cavity closure rate of 86.0% has been achieved. The number of bacterial colonies in lungs and spleens could be reduced. The number of bacterial colonies in lungs could be 19.5×104 CFU, and the number of the bacterial colonies in spleens could be 0.8×104 CFU.

The medicament of the present invention can increase the number of T lymphocytes CD4+T of mice, increase the thymus index of mice and increase the content of IFN-γ of multi-drug resistant tuberculosis mice. IFN-γ is the key of effective antibacterial immunity, which attract and gather monocytes/macrophagocytes to enhance its effect of killing the multi-drug resistant *Mycobacterium Tuberculosis*. The number of CD4+T could be 41.98/μL and the thymic weight index could be 0.328. In addition, the content of IFN-γ could be 77.23 ng/mL.

Embodiment 23

A Method for Preparing a Medicament for Use in Treating Tuberculosis

The Following Steps of the Method were Performed:

(1) Weighing weighing all the components according to the formula;

(2) Cleaning of Chinese Herbal Medicines cleaning all the Chinese herbal medicine components except for the glycoprotein;

(3) Extracting of Chinese Herbal Medicines adding the Chinese herbal medicines to clear water of 12 times of volume for soaking 1 h under the condition of 50 DEG C., then increasing the temperature to 60 DEG C. and the pressure to 29 kPa and carrying out ultrasonic-assisted extraction, with the ultrasonic power being 130 W, the ultrasonic frequency being 250 kHz, the treatment time being 4-5 s, and the chill time being 2-6 s; after one hour, filtering, collecting the filtrate, and carrying out spray-drying, thereby obtaining a Chinese herbal medicine powder;

(4) Adding of the Glycoprotein mixing the marine algal glycoprotein powder and the above Chinese herbal medicine powder uniformly, and then preparing the mixture into different dose forms, such as capsules, tablets and the like.

The medicament of the present invention has a pH of 5.3-9.8, preferably 6.5-7.5.

Lots of experiments were done on the present invention. Multiple experiments were done with the glycoproteins and mixtures of polysaccharides and proteins extracted from sea shells, bones of the livestock, and skeletons of marine animals, and the objectives of the present invention could also be achieved.

Embodiment 24

A Medicament for Use in Treating Tuberculosis

The medicament is a mixture of a polysaccharide and a protein;

the medicament comprises 1%-99% of polysaccharide and 1%-99% of protein by weight;

the polysaccharide comprises xylose, fucose, arabinose, glucose, galactose, mannose, and rhamnose;

the protein comprises asparagamide, cysteine, lysine, arginine, serine, threonine, alanine, aspartic acid, glutamine, glutamic acid, histidine, isoleucine, glycine, leucine, methionine, phenylalanine, proline, tyrosine and valine;

the molecular weight of polysaccharide in the mixture of polysaccharide and protein is 0.2-3000 kDa;

the molecular weight of protein in the mixture of algae polysaccharide and protein is 0.2-3000 kDa.

The mixture of polysaccharide and protein can become the mixture of algal polysaccharide and algal protein;

the mixture of algal polysaccharide and algal protein comprises pigment;

the pigment is a natural pigment contained in an algal substance;

the algal protein could be one of the phycocyanin, phycoerythrin, or the yellow-algal protein.

According to the Above Embodiments 13-18, an Experiment on Airway Hyperresponsiveness was Conducted, with an Experimental Method and Effects being Shown Below:

(1) mice for the experiment: the male mice for this experiment were 6 weeks old;

(2) dose: the dose for each mouse was 3 g/day, 3 times a day;

(3) antigen sensitization, allergy attack and treatment: 200 μg of conalbumin (CA) and 2 mg of dinitrobenzene (DNP)-bound albumin were dissolved in 0.3 ml of buffer solution PBS and then intrathecally injected into mice for sensitization twice at an interval of one week. The mice were anesthetized 7 days later after the second sensitization, and were intratracheally provided with 0.05 ml of buffer solution PBS containing 100 μg of conalbumin (CA) to induce an allergy attack. On the 20th day and the 30th day, a further allergy attack was induced by the same method at twice dose. The mice having an allergy attack were divided into 9 groups 24 hours later after the first allergy attack. Groups 1-6 were treated with the medicament as described in Embodiments 13-18 of the present invention that was intragastrically administrated by using a type 25 metering blunt stainless steel needle, 1 g each time and three times a day, continuously for 17 days. The mice having an allergy attack were divided into 9 groups 24 hours later after the first allergy attack. Groups 1-6 were treated with the medicament as described in Embodiments 13-18 of the present invention that was intragastrically administrated by using a type 25 metering blunt stainless steel needle, 1 g each time and three times a day, continuously for 17 days. Group 7 was treated with dexamethasone and intraperitoneally injected with 0.5 ml/kg dexamethasone every day. Group 8 served as a model control group and was intraperitoneally provided with saline solution every day. Group 9 was blank control group without any treatment;

(4) measurement of late-phase airway response: on the third day after the last allergy attack, the mice of the above 8 groups were intravenously injected with acetylcholine, and then the airway pressure changes of these mice and those of group 9 were all measured to reflect airway responses. The specific steps were as follows: anesthetizing the mice by using pentobarbital and keeping the respiratory tract unblocked by using an 18# endotracheal tube; keeping 120 breaths per minute by using an RSP 1002 type pressure controllable respiratory system, and keeping the tidal volume constant at 0.2 ml; intravenously injecting dodecyl ammonium bromide into each mouse by 25 mg/kg to induce muscle relaxation; connecting a pressure transducer to the endotracheal tube to measure the airway pressure; intravenously injecting acetyl choline into each mouse by 50 μg/kg after the airway pressure was stabilized for 2 minutes, observing and recording the airway pressure changes in 4 minutes by using a VENTP software system, calculating the time of airway pressure peaks with reference to airway pressure-time index (APTI) (centimeter water column per second), combining changes to reflect the airway responses. The measured specific values are shown in table 7.

TABLE 7

| Group | Number of mice | APTI (centimeter water column per second) |
| --- | --- | --- |
| Embodiment 13 | 15 | 600 ± 23 |
| Embodiment 14 | 15 | 534 ± 24 |
| Embodiment 15 | 15 | 613 ± 22 |
| Embodiment 16 | 15 | 580 ± 25 |
| Embodiment 17 | 15 | 480 ± 27 |
| Embodiment 18 | 15 | 595 ± 31 |
| Group treated with dexamethasone | 15 | 565 ± 31 |
| Model control group | 15 | 1245 ± 110 |
| Blank control group | 15 | 430 ± 26 |

The airway pressure-time index (APTI) levels of the groups treated with the medicament as described in Embodiments 13-18 of the present invention and dexamethasone were significantly lower than that of the model control group. There was no significant difference between the groups treated with the medicament of the present invention and the group treated with dexamethasone, and the airway hyperresponsibility could be completely eliminated.

The no-toxic-effect dose of the medicament of the present invention for oral administration to dogs for 12 weeks was 1.6 g/kg, which was equivalent to 50 times the equivalent dose for human. Therefore, it would be believed that the safety of clinical trials could be guaranteed.

The medicine described in the invention can also be a health care product or a food.

The basic principles and main features of the present invention and the advantages of the present invention are shown and described above. It should be understood by those skilled in the art that the present invention is not limited by the Embodiments described above. The descriptions of the above Embodiments and the description are merely illustrative of the principles of the present invention. Various variations and modifications can be made to the invention without departing from the spirit and scope of the invention. Such variations and modifications all fall within the scope of the claimed invention. The scope of the present invention is defined by the appended claims and their equivalents.

What is claimed is:

1. A medicament for use in treating tuberculosis, comprising: a marine algae glycoprotein, indigo naturalis, dioscorea nipponica, and glucuronic acid in a ratio of 1:5:6:1 by weight,
wherein, the marine algae glycoprotein is obtained from *Nostoc flagelliforme*, and comprises 26% saccharide and 74% protein by weight with a molecular weight of 8 kDa.

* * * * *